(12) United States Patent
Aoki et al.

(10) Patent No.: US 8,685,952 B2
(45) Date of Patent: Apr. 1, 2014

(54) METHOD FOR THE TREATMENT OF DIABETES

(75) Inventors: Taro Aoki, Tokorozawa (JP); Katsutoshi Miyosawa, Higashimurayama (JP)

(73) Assignees: KOWA Co., Ltd., Nagoya-shi (JP); Nissan Chemical Industries, Ltd., Tokyo (JP)

( * ) Notice: Subject to any disclaimer, the term of this patent is extended or adjusted under 35 U.S.C. 154(b) by 1984 days.

(21) Appl. No.: 11/476,873

(22) Filed: Jun. 29, 2006

(65) Prior Publication Data
US 2007/0179194 A1 Aug. 2, 2007

(30) Foreign Application Priority Data
Jan. 31, 2006 (JP) .................................. 2006-21817

(51) Int. Cl.
*A01N 43/00* (2006.01)
*A61K 31/33* (2006.01)
*A01N 37/02* (2006.01)
*A01N 37/06* (2006.01)
*A61K 31/225* (2006.01)

(52) U.S. Cl.
USPC .......................................... 514/183; 514/548

(58) Field of Classification Search
USPC ................................................ 514/183, 548
See application file for complete search history.

(56) References Cited

U.S. PATENT DOCUMENTS 5,856,336 A   1/1999   Fujikawa et al.

FOREIGN PATENT DOCUMENTS

| CN | 1440283 A | 9/2003 |
| JP | 2003-530342 | 10/2003 |
| JP | 2004-519424 | 7/2004 |
| WO | WO 01/76573 | 10/2001 |
| WO | WO 02/15892 | 2/2002 |
| WO | WO 2004/096276 | * 11/2004 |
| WO | WO 2004/096276 A1 | 11/2004 |

OTHER PUBLICATIONS

Tsujii et. al. (Current Therapeutic Research (1998) 59:863-872).*
Bastin et. al. (Organic Process Research and Development (2000) 4:427-435).*
Goodman and Gilman's The Pharmacological Basis of Therapeutics (Tenth Edition (2001), McGraw Hill, Chapter I, pp. 3-29).*
Jürgen M. Lehmann, et al., "An Antidiabetic Thiazolidinedione Is a High Affinity Ligand for Peroxisome Proliferator-activated Receptor γ(PPARγ)*", The Journal of Biological Chemistry, vol. 270, No. 22, Jun. 2, 1995, pp. 12953-12956.
Jean-Louis Chiasson, et al., "Acarbose for prevention of type 2 diabetes mellitus: the STOP-NIDDM randomized trial", The Lancet, vol. 359, Jun. 15, 2002, pp. 2072-2076.
Kouji Kajinami, et al., "Pitavastatin: Efficacy and Safety Profiles of A Novel Synthetic HMG-CoA Reductase Inhibitor", Cardiovascular Drug Reviews, vol. 21, No. 3, 2003, pp. 199-215.
"HMG-CoA Reductase Inhibitor, Pitavastatin", Therapeutic Research, vol. 24, No. 7, Jul. 2003, pp. 1329-1337. (with partial English translation).
Hakan Tezcan, et al., "Effect of angiotensin-converting enzyme inhibition on endothelial function and insulin sensitivity in hypertensive patients", Journal of Renin-Angiotensin-Aldosterone System, vol. 4, No. 2, Jun. 2003, pp. 119-123.
Tetsuya Shiuchi, et al., "ACE Inhibitor Improves Insulin Resistance in Diabetic Mouse Via Bradykinin and NO", Hypertension, vol. 40, No. 329, Jul. 29, 2002, 18 Pages.
Office Action issued May 8, 2012, in Japanese Patent Application No. 2007-556799, (with English-language Translation).

* cited by examiner

*Primary Examiner* — Marcos Sznaidman
(74) *Attorney, Agent, or Firm* — Oblon, Spivak, McClelland, Maier & Neustadt, L.L.P.

(57) ABSTRACT

The present invention provides a method for treatment of diabetes, comprising administering a pitavastatin, and in combination therewith, enalapril or a salt thereof.

8 Claims, 2 Drawing Sheets

METHOD FOR THE TREATMENT OF DIABETES

BACKGROUND OF THE INVENTION

1. Field of the Invention

The present invention relates to a method for the treatment of diabetes, which method produces excellent effect of reducing insulin resistance.

2. Background Art

Type II diabetes is a disease exhibiting anomalous glucose tolerance; i.e., high insulin resistance, and the number of patients of diabetes has increased in recent years as a result of lifestyle-related factors such as obesity and overeating. Such patients currently number 7,400,000 in Japan and 150,000,000 throughout the world, and will probably reach 300,000,000 in 2005. Insulin resistance is a state in which insulin-interacting cells exhibit decreased sensitivity to insulin. Increase in insulin resistance is known to cause type II diabetes and have close relation to the onset of hypertension and progress of arteriosclerosis.

Thiazolidines are typical agents which are effective in overcoming insulin resistance. It has been known that when such thiazolidines typified by rosiglitazone or pioglitazone are attached to PPARγ, which is a nuclear receptor, PPARγ is activated, whereby adipose cells are differentiated (J. Biol. Chem. 270, 12953 to 12956 (1995)). However, thiazolidine-based drugs exhibit adverse side effects such as toxicity to the liver, edema, and increase in body weight. Thus, in the treatment of diabetes, a thiazolidine-based drug has been used as an auxiliary medicine to be administered along with a sulfonylurea drug.

In general, diabetes patients often suffer from other diseases. Therefore, reducing or ameliorating insulin resistance is important not only in the treatment of diabetes but also for other pathological conditions. For example, patients of hyperlipemia often exhibit hyperglycemia in relation to insulin resistance. Such patients must be treated for overcoming anomalous lipid metabolism and reducing insulin resistance. As has already been described in literature, α-glycosidase, serving as an oral hypoglycemic agent, remarkably reduces the risk of the onset of heart infarction by virtue of the insulin resistance reduction effect thereof (Lancet, (2002), 359:2072), suggesting that a combined treatment targeting anomalous lipid metabolism and high insulin resistance would be promising treatment. As mentioned above, since thiazolidine-based drugs exhibit adverse side effects such as toxicity to the liver and increase in body weight, other insulin resistance reducing agents that are safer and more effective are demanded in the therapy of hyperlipemia.

Meanwhile, Pitavastatin (i.e., 3-hydroxy-3-methylglutalyl-CoA (HMG-CoA) reductase inhibitor), which is a first choice drug for hyperlipemia (disclosed in JP-B-2569746, U.S. Pat. No. 5,856,336, and EP Patent No. 304063), is known to exhibit an effective blood cholesterol reducing effect in basic research and in clinical settings, as reported in Cardiovasc. Drug Rev. (2003) 21(3), 199 to 215. Meanwhile, pitavastatin exhibits an effect of improving impaired glucose tolerance (insulin resistance reducing effect) in KKAy mice, which are type II diabetes model mice (Therapeutic Research (0289-8020) vol. 24, No. 7, p. 1329-1337 (2003.07)). WO2004/096276 discloses that pravastatin, which is an HMG-CoA reductase inhibitor, also exhibits an effect of reversing impaired glucose tolerance in KKAy mice. However, improvement of the above-obtained effects in overcoming impaired glucose tolerance is still required.

As described above, for the hyperlipemia patients suffering hyperlipemia concomitant with insulin-resistance-related hyperglycemia, in addition to anomalous lipid metabolism, insulin resistance must be properly controlled. However, hitherto, a useful method for the composite treatment of anomalous lipid metabolism and high insulin resistance has never been known.

An object of the present invention is to provide method for treating diabetes having reduced side effect which exhibits excellent ameliorating effect for insulin resistance.

SUMMRY OF THE INVENTION

In view of the foregoing, the present inventors have conducted extensive studies, and have found that, among HMG-CoA reductase inhibitors, combined use of pravastatin and enalapril maleate serving as an ACE inhibitor only exhibits an effect of improving impaired glucose tolerance almost equivalent to that obtained when each drug component is administered singly; however, when pitavastatin and enalapril maleate are used in combination, the effect of improving impaired glucose tolerance is remarkably enhanced, and the combined use is beneficial for improving anomalous lipid metabolism and reducing insulin resistance as well. The present invention has been accomplished on the basis of these findings.

Some angiotensin converting enzyme (ACE) inhibitors, serving as hypertension treatment drugs, are known to exhibit an insulin resistance reducing effect. For example, JRAAS (2003), 4(2), 119 to 123 discloses a hypotensive effect and an insulin resistance reducing effect provided by enalapril maleate, and Hypertension, 2002; 40:329 discloses reduction of insulin resistance of KKAy mice in the glucose tolerance test employing temocapril. However, hitherto, there has never been reported combined use of an HMG-CoA reductase inhibitor and an ACE inhibitor as a new method for improving anomalous lipid metabolism and impaired glucose tolerance. In addition, the combined effect on impaired glucose tolerance (diabetes) obtained through use of these two drug components in combination has never been conceived by those skilled in the art. More specifically, the combined effect on impaired glucose tolerance obtained through use of pitavastatin and enalapril maleate in combination has never been known to those skilled in the art.

Accordingly, the present invention provides a method for treatment of diabetes, comprising administering a pitavastatin, and in combination therewith, enalapril or a salt thereof.

An excellent improving effect on impaired glucose tolerance (i.e., improving effect on insulin resistance) is obtainable by the treatment method of the present invention, and it is useful for treatment of diabetes, especially type II diabetes. Moreover, a combinational therapy targeting anomalous lipid metabolism and impaired glucose tolerance of a patient of hyperlipemia who is simultaneously suffered from hyperglycemia due to insulin resistance becomes possible

DETAILED DESCRIPTION OF PREFERRED EMBODIMENTS

Figure 1:
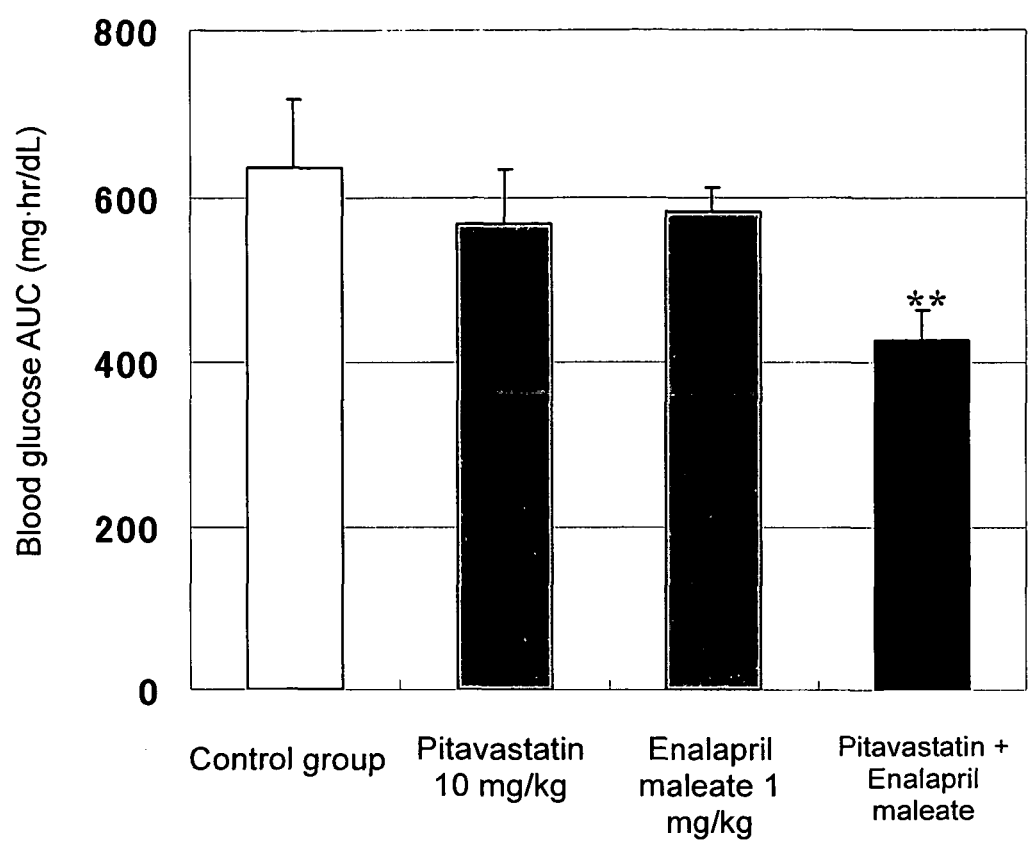
FIG. 1 is a graph showing an AUC (area under the curve) of blood glucose level when pitavastatin calcium (represented by pitavastatin) and enalapril maleate were administered in combination.

As used herein, the word "pitavastatin" collectively refers to pitavastatin per se, a salt thereof, and a lactone-formed species thereof. Hydrates and solvates formed with a pharmaceutically acceptable solvent also fall within the scope of pitavastatin. Pitavastatin exhibits a cholesterol synthesis inhibitory activity on the basis of an HMG-CoA reductase inhibitor and is known as a hyperlipemia treatment drug. Examples of the salts of pitavastatin include alkali metal salts such as sodium salts and potassium salts; alkaline earth metal salts such as calcium salts and magnesium salts; organic amine salts such as phenetylamine salts; and ammonium salts. Among the above pitavastatin species, pitavastatin salts are preferred, with calcium salts and sodium salts being particularly preferred.

Pitavastatin and related species thereof may be produced through a method disclosed in U.S. Pat. No. 5,856,336 or JP-A-1989-279866.

Enalapril, employed in the present invention, is an ACE inhibitor and readily available as a commercial product. No particular limitation is imposed on the salt of enalapril so long as the salt is pharmacologically acceptable. Examples of the salt include inorganic acid salts such as hydrochloride, sulfate, nitrate, hydrobromide, and phosphate, and organic acid salts such as acetate, trifluoroacetate, fumalate, maleate, lactate, tartrate, citrate, succinate, malonate, methanesulfonate, and p-toluenesulfonate. Of these, maleate is preferred.

According to the present invention, a pitavastatin, and enalapril or a salt thereof are administered in combination. As shown in the Example hereinbelow, combined administration has yielded a remarkable improvement in the impaired glucose tolerance in KKAy mice, as compared with sole administration of a pitavastatin or sole administration of enalapril or a salt thereof.

A KKAy mouse is a model for type II diabetes. Thus, the effect of a drug on improvement of impaired glucose tolerance (reduction of insulin resistance) can be evaluated on the basis of the degree of improvement of impaired glucose tolerance of KKAy mice. Therefore, the method of the present invention is useful for the treatment of a disease characterized by impaired glucose tolerance, particularly for the treatment of type II diabetes.

In the present invention, the formulation of a pitavastatin, and enalapril or a salt thereof may be appropriately selected in consideration of the condition of a patient or other factors. For example, the formulation may be any of powder, granules, dry syrup, tablets, capsules, and injections. These formulations may be produced through any production method known in the art by admixing a pharmaceutically acceptable carrier with a pitavastatin, and enalapril or a salt thereof.

In manufacture of oral solid preparations, the two drug components are admixed with a vehicle and, in accordance with needs, additives such as a binder, a disintegrant, a lubricant, a colorant, a flavoring agent, and an aroma. Various formulations such as tablets, granules, powder, and capsules may be produced from the mixture through a routine method. Additives generally employed in the art may be used as the above additives. Examples of the vehicle include lactose, sodium chloride, glucose, starch, microcrystalline cellulose, and silicic acid. Examples of the binder include water, ethanol, propanol, simple syrup, liquid gelatin, hydroxypropyl cellulose, methyl cellulose, ethyl cellulose, Shellac, calcium phosphate, and poly(vinylpyrrolidone). Examples of the disintegrant include agar powder, sodium hydrogencarbonate, sodium lauryl sulfate, and stearic monoglyceride. Examples of the lubricant include refined talc, stearate salts, borax, and polyethylene glycol. Examples of the colorant include β-carotene, yellow iron sesquioxide, and caramel. Examples of the flavoring agent include white sugar and bitter orange peel.

In manufacture of oral liquid preparations, the two drug components are admixed with additives such as a flavoring agent, a buffer, a stabilizer, and a preservative. Various formulations such as oral liquids, syrups, and elixirs may be produced from the mixture through a routine method. Additives generally employed in the art may be used as the above additives. Examples of the flavoring agent include white sugar. Examples of the buffer include sodium citrate. Examples of the stabilizer include traganth. Examples of the preservative include paraoxybenzoate esters.

In manufacture of injections, the two drug components are admixed with additives such as a pH-regulator, a stabilizer, and a tonicity agent. Various formulations such as subcutaneous injections, intramuscular injections, and intravenous injections may be produced from the mixture through a routine method. Additives generally employed in the art may be used as the above additives. Examples of the pH-regulator include sodium phosphate. Examples of the stabilizer include sodium pyrosulfite. Examples of the tonicity agent include sodium chloride.

In the treatment method according to the present invention, no particular limitation is imposed on the administration mode of a pitavastatin and enalapril (or a enalapril salt). Specifically, two drug components may be administered simultaneously or separately with an interval. In other words, a pitavastatin and enalapril (or an enelapril salt) may be formulated as a single preparation. Alternatively, two components may be separately formulated to provide corresponding preparations for producing a kit. In the latter case, two preparations may have different physical shapes. Frequency of administration of a pitavastatin may differ from that of enalapril or a salt thereof.

According to the present invention, when two components are contained in a single preparation, and such a preparation is administered to a patient in need thereof, a pitavastatin and enalapril (or an enalapril salt) are preferably formulated at a ratio by mass of 1:0.05 to 1:50, more preferably 1:0.1 to 1:10.

In the present invention, the dose of each drug component is suitably selected in consideration of the symptoms. The dose of pitavastatin is 0.1 to 50 mg per day, preferably 1 to 20 mg per day. The dose of enalapril or a salt thereof is 1 to 50 mg per day, preferably 2.5 to 20 mg per day. Two components may be administered once a day or two or more times a day in a divided manner.

EXAMPLES

The present invention will next be described in detail by way of examples, which should not be construed as limiting the invention thereto.

Example 1

Effects of combined administration of pitavastatin calcium (hereinafter referred to simply as pitavastatin) and enalapril maleate on impaired glucose tolerance were evaluated through the following test procedure.

1. Tested Animal and Breeding Environment

Male KKAy mice (age: 10 weeks, Nippon Cler Co., Ltd.) were provided. Throughout the duration of the experiment, the mice were housed in a cage with a controlled light/dark cycle (duration of light period with a room light: 7:00 a.m. to 7:00 p.m.) at a temperature of 23±3° C. and a humidity of 55±15% and were allowed to freely take a solid chow (CE-2; Nippon Cler Co., Ltd.) and tap water.

2. Drug Preparation

Pitavastatin and/or enalapril maleate were suspended in a 0.5-mass % aqueous solution of carboxymethyl cellulose (Iwai Kagaku Co., Ltd.) so that the pitavastatin content and the enalapril maleate content were adjusted to 1 mg/mL and 0.1 mg/mL, respectively. Since pitavastatin has a water content of 9.43%, pitavastatin was weighed in an amount of 1.1 times by mass the target dose for compensation. The suspension was refrigerated (4° C.) in a light-tight bottle. The suspensions were prepared every 7 days.

3. Test Method

Twenty four KKAy mice were randomly divided into the following four groups (six mice per group): a control group, a pitavastatin alone (10 mg/kg) group, an enalapril maleate alone (1 mg/kg) group, and a pitavastatin (10 mg/kg) and enalapril maleate (1 mg/kg) combined use group. Each of pitavastatin and enalapril maleate was orally administered once a day at a dose of 10 mL/kg for 21 days, and a 0.5 mass % aqueous sodium carboxymethyl cellulose solution (10 mL/kg) was orally administered to the control group. In all groups, the oral glucose tolerance test was performed after fasting for 18 hours following the final administration. Specifically, the tail of each mouse was cut (about 3 mm from the tip), thereby collecting blood from the tail vein. Immediately after collection, blood glucose level was determined by means of a medisafe reader (GR-101, product of Terumo Co., Ltd.). After determination of the initial blood glucose level, an aqueous glucose solution was orally administered to each mouse (2 g/10 mL/kg), and blood glucose level was determined in a similar manner at 15, 30, 60, and 120 minutes after administration of glucose. In each group, AUC of blood glucose level was calculated.

4. Statistical Analysis and Data Processing Method

The differences between the control group and the drug-administered groups were analyzed on the basis of Dunnett's multiple comparison test, preceded by Bartlett's analysis of variance. Significance levels less than 5% were considered to indicate statistically significant results.

5. Results

FIG. 1 shows an AUC of blood glucose level (to glucose tolerance hour 2). The AUC of blood glucose level represents the total amount of blood glucose. Therefore, a decrease in AUC is considered to indicate improvement of impaired glucose tolerance.

Comparative Example 1

The evaluation procedure of Example 1 was repeated, except that pravastatin sodium (hereinafter referred to simply as pravastatin) (50 mg/kg) was used instead of pitavastatin. Pravastatin (50 mg/kg) has a blood cholesterol level reducing effect almost equivalent to that of pitavastatin (10 mg/kg).

1. Drug Preparation

The procedure of Example 1 was repeated, except that the pravastatin content was adjusted to 5 mg/mL, whereby a drug was prepared.

2. Test Method

Testing was performed in a manner similar to that of Example 1. However, twenty four KKAy mice were randomly divided into the following four groups (six mice per group): a control group, a pravastatin alone (50 mg/kg) group, an enalapril maleate alone (1 mg/kg) group, and a pravastatin (50 mg/kg) and enalapril maleate (1 mg/kg) combined use group.

3. Statistical Analysis and Data Processing Method

Statistical Analysis and Data Processing are performed in a manner similar to that of Example 1.

4. Results

Figure 2:
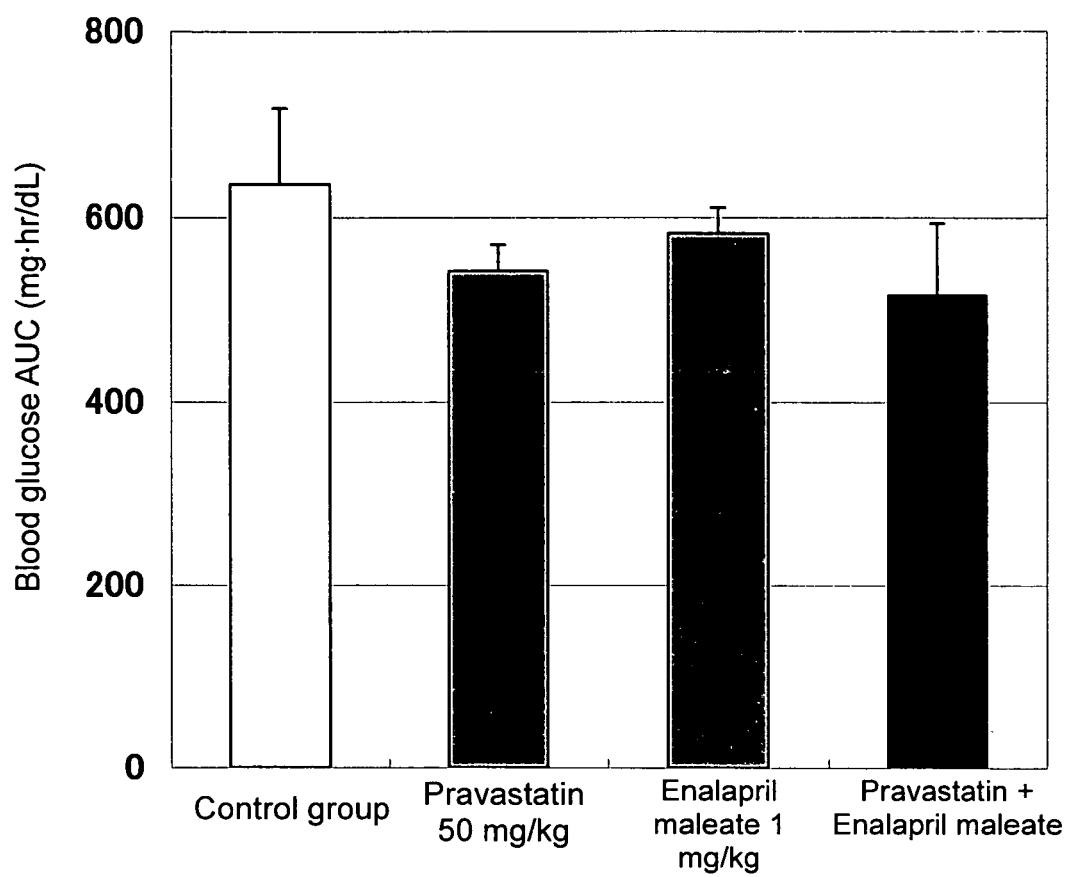
FIG. 2 is a graph showing an AUC of blood glucose level when pravastatin sodium (represented by pravastatin) and enalapril maleate were administered in combination.

FIG. 2 shows an AUC of blood glucose level (to glucose tolerance hour 2).

The test results are summarized as follows.

AUC of blood glucose level tended to be reduced in the pitavastatin alone group, the pravastatin alone group, and the enalapril maleate alone group, as compared with the control group. The pravastatin and enalapril maleate combined administration group exhibited no combination effect, and the AUC tended to be reduced. In contrast, the pitavastatin and enalapril maleate combined administration group exhibited a considerable decrease in AUC as compared with the single administration groups. That is, impaired glucose tolerance was considerably improved ($P<0.05$), and the effect was found to be synergistic (relative index of the pitavastatin-enalapril maleate combined administration group (0.67) <product of relative index of the pitavastatin alone group and that of the enalapril maleate alone group (0.82)).

Accordingly, administration of pitavastatin and enalapril maleate in combination according to the present invention was found to exhibit a remarkable effect of improving impaired glucose tolerance, as compared with administration of another HMG-CoA reductase inhibitor and enalapril maleate in combination.

What is claimed is:

1. A method for treatment of diabetes, comprising administering an effective amount of pitavastatin calcium and an effective amount of enalapril maleate to a subject in need of such treatment.

2. The method of claim 1, wherein the diabetes is type II diabetes caused by an increase in insulin resistance.

3. The method of claim 1, wherein administering an effective amount of pitavastatin calcium and an effective amount of enalapril maleate comprises administering a composition comprising pitavastatin calcium and enalapril maleate.

4. The method of claim 3, wherein a mass ratio of pitavastatin calcium to enalapril maleate in the composition is from 1:0.05 to 1:50.

5. The method of claim 3, wherein a mass ratio of pitavastatin calcium to enalapril maleate in the composition is from 1:0.1 to 1:10.

6. The method of claim 1, wherein administering an effective amount of pitavastatin calcium and an effective amount of enalapril maleate comprises:
administering 0.1 to 50 mg per day of pitavastatin calcium; and
administering 1 to 50 mg per day of enalapril maleate.

7. The method of claim 1, wherein administering an effective amount of pitavastatin calcium and an effective amount of enalapril maleate comprises:
administering 1 to 20 mg per day of pitavastatin calcium; and
administering 2.5 to 20 mg per day of enalapril maleate.

8. The method of claim 1, wherein administering an effective amount of pitavastatin calcium and an effective amount of enalapril maleate comprises:
administering pitavastatin calcium at a dosage of 10 mg/kg/day; and
administering enalapril maleate at a dosage of 1 mg/kg/day.

* * * * *